(12) United States Patent
Burba (10) Patent No.: US 9,121,793 B2
(45) Date of Patent: Sep. 1, 2015

(54) SEMI-OPEN-PATH GAS ANALYSIS SYSTEMS AND METHODS

(75) Inventor: George G. Burba, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 497 days.

(21) Appl. No.: 13/426,492

(22) Filed: Mar. 21, 2012

(65) Prior Publication Data
US 2013/0250304 A1    Sep. 26, 2013

(51) Int. Cl.
| G01N 21/59 | (2006.01) |
| G01N 1/22 | (2006.01) |
| G01N 21/3504 | (2014.01) |
| G01N 21/05 | (2006.01) |
| G01N 1/24 | (2006.01) |

(52) U.S. Cl.
CPC .............. G01N 1/2273 (2013.01); G01N 21/05 (2013.01); G01N 21/3504 (2013.01); G01N 2001/245 (2013.01)

(58) Field of Classification Search
CPC . G01N 21/3504; G01N 21/05; G01N 21/276; G01N 1/2273; G01N 2001/245
USPC .............. 356/342, 347, 72–73; 250/343, 345, 250/338.5
See application file for complete search history.

(56) References Cited

U.S. PATENT DOCUMENTS

| 4,225,243 | A | * | 9/1980 | Typpo ............................ 356/409 |
| 4,288,062 | A | * | 9/1981 | Gupta et al. ..................... 266/88 |
| 4,413,911 | A | * | 11/1983 | Rice et al. ...................... 356/438 |
| 5,067,356 | A | | 11/1991 | Businger |
| 5,282,473 | A | * | 2/1994 | Braig et al. .................... 600/532 |
| 5,610,400 | A | * | 3/1997 | Weckstrom ................... 250/345 |
| 5,621,213 | A | * | 4/1997 | Barshad ........................ 250/373 |
| 6,279,378 | B1 | * | 8/2001 | Sheen et al. ................. 73/24.01 |
| 6,317,212 | B1 | * | 11/2001 | Eckles .......................... 356/437 |
| 6,527,398 | B1 | * | 3/2003 | Fetzer .......................... 356/437 |

(Continued)

FOREIGN PATENT DOCUMENTS

WO    WO 2011/130320 A2    10/2011

OTHER PUBLICATIONS

Darmais, S. et al., "Emission fluxes of VOC by orange trees determined by both relaxed eddy accumulation and vertical gradient approaches," Chemosphere: Global Change Science, (2000), vol. 2, No. 1, pp. 47-56.

(Continued)

*Primary Examiner* — Sang Nguyen
(74) *Attorney, Agent, or Firm* — Gerald T. Gray; Leydig, Voit & Mayer (57) ABSTRACT

A gas analyzer includes a detector section including a detector, a source section including a light source, and a support structure coupling the detector section with the source section and forming a flow channel defining an optical path measuring region. The gas analyzer also includes an air flow device configured to pull air through the flow channel from an intake region in the support structure to an exhaust region. Sampling is done by pulling air into the sampling cell via an intake opening or tube of wide diameter and short to medium at very fast flow rates (e.g., 10-3000 lpm or more) enabling rapid gas sampling. Fast flow rates enable the use of large volume cell for rapid gas sampling, which in turn, enables rapid measurements of many low-concentration trace gases and sticky/reactive gases (e.g., methane, ammonia, isotopes of $CO_2$, $H_2O$, nitrous oxide, etc.).

20 Claims, 4 Drawing Sheets

(56) References Cited

U.S. PATENT DOCUMENTS

| | | | |
|---|---|---|---|
| 8,125,626 B2* | 2/2012 | Furtaw | 356/72 |
| 2001/0048079 A1* | 12/2001 | Brunamoti et al. | 250/343 |

OTHER PUBLICATIONS

Grönholm, Tiia et al., "The dependence of the $\beta$ coefficient of REA system with dynamic deadband on atmospheric conditions," Environmental Polution, (2008), vol. 152, No. 3, pp. 597-603.

Ueyama, Masahito et al., "Continuous measurement of methane flux over a larch forest using a relaxed eddy accumulation method," Theoretical and Applied Climatology, (2012), vol. 109, No. 3-4, pp. 461-472.

"CPEC200 Closed-Path Eddy-Covariance Flux System," Campbell Scientific, Inc. Publication, Copyright 2011, 2012, Printed Apr. 2012 (3 pages).

"EC155 CO2 and H2O Closed-Path Gas Analyzer and EC100 Electronics with Optional CSAT3A 3D Sonic Anemometer Revision: 8/11 Instruction Manual," Campbell Scientific, Inc. Publication, Copyright 2010-2011 (63 pages).

Sargent, Steve and Kim, Hongcheol, "Frequency Response of a Low-Power Closed-Path CO2 and H2O Eddy Covariance System," Campbell Scientific, Inc. (1 page).

TGA 100 Trace Gas Analyzer User and Reference Manual, Aug. 2, 2004, Campbell Scientific, Inc.

LI-7500 CO2/H2O Analyzer Instructions Manual, Complete Manual 155 pages, Jan. 2004, United States.

Burba, G.G. et al., Novel Design of an Enclose CO2/H2O Gas Analyzer for Eddy Covariance Flux Measurements,, pp. 743-748, 2010. Tellus: Series B Chemical and Physical Meteorology, vol. 62B, International Meteorological Institute in Stockholm.

Clement R.J. et al., Improved Trace Gas Flux Estimation Through IRGA Sampling Optimization, pp. 623-638, 2009, Agricultural and Forest Meteorology, vol. 149, Elsevier B.V.

Brach, E.J, et al., Open Path CO2 Analyzer, pp. 1415-1419, 1981, Journal of Phys. E: Sci. Instrum. vol. 14, IOP Publishing, Great Britain.

EC155 CO2, and H2O Closed-Path Gas Analyzer and EC100 Electronics with Optional CSAT3A 3D Sonic Anemometer, Complete Manual 58 pages, Feb. 2011, United State.

Grelle, Achim et. al., Fine-Wire Thermometer to Correct CO2 Fluxes by Open-Path Analyzers for Artificial Density Fluctuations, pp. 48-57, 2007, Agricultural and Forest Meteorology, vol. 147, Elsevier, B.V.

Brodeur, J.J. et al., Technical Note: Laboratory Evaluation of Tunable Diode Laser System for Eddy Covariance Measurements of Ammonia Flux, pp. 385-391, Feb. 2009, Agricultural and Forest Meteorology, vol. 149, Elsevier B.V.

* cited by examiner

SEMI-OPEN-PATH GAS ANALYSIS SYSTEMS AND METHODS

CROSS-REFERENCES TO RELATED APPLICATIONS

NOT APPLICABLE

STATEMENT AS TO RIGHTS TO INVENTIONS MADE UNDER FEDERALLY SPONSORED RESEARCH OR DEVELOPMENT

NOT APPLICABLE

BACKGROUND

The present invention relates generally to gas analysis, and more particularly to systems and methods for measuring concentrations of gases, including low-concentration or trace gases in the atmosphere.

The increasing concentrations of carbon dioxide and other trace gases in the atmosphere and the resulting greenhouse effect and climate change have become important topics for scientific research. In order to understand the global carbon balance, it is necessary to determine the rate at which carbon dioxide, other trace gases and energy exchanges occur between the atmosphere and terrestrial and oceanic ecosystems. A measurement technique called "eddy covariance" has been widely used to determine these rates. The air within a few hundred meters above the earth surface is mostly turbulent, so that turbulent structures (vortices of variable sizes) called "eddies" are responsible for the vertical transport of the most of the gases, including carbon dioxide, other trace gases, and water vapor, and also heat and momentum between the surface and the atmosphere. The rates of such transport can be calculated from simultaneous, high-frequency measurements of the vertical component of wind speed, the concentrations of carbon dioxide, or other trace gases, and water vapor and air temperature.

To measure concentrations of carbon dioxide, other trace gases, and water vapor, a gas analyzer can be used to analyze the transmittance of light in appropriate wavelength bands through a gas sample. With some gas analyzers, a sample gas containing unknown concentrations of a sampled gas and water vapor is placed in a sample cell, and a reference gas with zero or known concentrations of this gas and water vapor is placed in a reference cell. The analyzer measures the unknown gas concentrations in the sample cell from calibrated signals that are proportional to the difference between light transmitted through the sample cell and light transmitted through the reference cell. Other similar methods have also been used utilizing a non-absorbent optical filter and a chopper motor to emulate a zero (no absorbing) condition, and no reference cell then is required.

Presently, readily available laser technologies are generally not able to provide enough resolution required for sampling of low-concentration gases unless substantial averaging is applied to minimize errors and to achieve required specifications, or a significant pressure drop in the sample cell is used to spectroscopically enhance the absorption lines. Atmospheric trace gases of low concentrations (e.g., $CH_4$, $N_2O$, $NH_3$, isotopes of $CO_2$ and $H_2O$, etc.). are therefore presently sampled in two major ways:

(I) slow sampling, when specifications are achieved by minimizing errors in measured concentrations by time-averaging; these may include flask, chamber, and mean concentration measurements; and (II) fast sampling, when errors in measured concentrations are reduced by averaging out in a large sampling volume and/or over long optical sampling paths. In both cases a significant pressure drop in the sampling cell is typically utilized to spectroscopically enhance the absorption lines.

The second, fast sampling approach is achieved in presently available instruments by either (II.a) using large sampling cell to allow the laser beam to pass through a large distance to be absorbed by a gas of interest, or (II.b) by the use of cavity ring down or related techniques that require very long optical paths (e,g, meters to kilometers) folded multiple times in a smaller high finesse cavity, which is highly sensitive to contamination, and can be impractical. The large sampling cell approach (II.a) presently requires very large flow in order to flush sample cell about 5-10 times per second (5-10 Hz) or more. Presently such flow is achieved by using a very powerful pump pulling air through the closed-path cell with a small intake opening (e.g., typically on the order of 0.5-1.0 cm) at 10-20× pressure drops. In both cases (II.a and II.b), the devices have high power demand, high maintenance requirements and unclear/uninvestigated consequences for measuring rapid gas fluctuations at $\frac{1}{10}$ to $\frac{1}{20}$ of the actual ambient air pressure.

In addition, reactive gases (e.g., volatile organic compounds, etc.) and "sticky" gases, (e.g., ammonia) are very difficult to sample using traditional intake tubes as are present on most prior art devices as initial information is lost due to chemical reactions or smearing while traveling through the intake tube.

Therefore it is desirable to provide systems and methods that overcome the above and other problems.

BRIEF SUMMARY

Systems and methods are provided for measuring concentrations of gases and in particular sticky and reactive gases. According to various embodiments, device configurations are provided that overcome some or all of the above problems and that allow rapid sampling in large cells at high flow rates with minimal or no flow restrictions, minimal or no intake structures, and minimal pressure drop, resulting in a significantly lowered power requirement. Various embodiments also allow for sampling of sticky gases (such as ammonia, etc.) and highly reactive gases (volatile organic compounds etc.), which currently are not sampled rapidly at all, or sampled inadequately through narrow intake tubes with large area-to-volume ratios leading to smearing of rapid information in the tube, and to loss of information due to physical and chemical reactions between tube walls and the gas.

According to various embodiments, systems and methods are provided that enable rapid (e.g., 5-10 Hz or greater) measurements of gas concentrations simultaneously with rapid measurements of the pressure and temperature of the sampled gas. In addition, devices according to various embodiments can advantageously use substantially lower power consumption.

Methods and devices are provided that enable rapid sampling of gas concentrations in a semi-open sampling cell of small to large volume. Sampling is done by pulling air into the sampling cell via one or more openings in the cell walls or via an intake tube of wide diameter and short to medium length (e.g., centimeters to decimeters). The openings in the cell wall or intake tube need to be wide, for example having a diameter comparable to, and of the same order of magnitude as the desired sampling cell diameter, ranging from 0.5 cm to many cm. Air is pulled through the wide intake and through the sampling cell at very fast flow rates (e.g., 10-3000 lpm or more) enabling rapid gas sampling. Fast flow rates enable the use of large volume cell for rapid gas sampling. The large volume cell, in turn, advantageously enables rapid measurements of many low-concentration trace gases (e.g., $CO_2$, $CH_4$, $N_2O$, $NH_3$, isotopes of $CO_2$ and $H_2O$, etc.) using available laser technologies, or other optical technologies, in a practical and relatively inexpensive way. Wide and short intake tubes, or windows or apertures in the sample cell walls, also advantageously enable sampling of sticky and reactive gases (such as ammonia, and various volatile components), because the volume to area ratio of the intake is small and the flow is fast. The minimal flow restriction and pressure drop advantageously allows for the use of a low-power device such as a fan, or a blower, in a low-power configuration. In certain aspects, simultaneously with rapid measurements of gases of interest, water vapor, air pressure and temperature of the sampled gas are also measured and can be used, for example, to correct for density fluctuations in the sampled gas.

According to one embodiment, a gas analyzer is provided that typically includes a detector section including a detector, a source section including a light source, and a support structure coupling the detector section with the source section and forming a flow channel defining an optical path measuring region. The gas analyzer also typically includes an air flow device configured to pull, or push, air through the flow channel from an intake region in the support structure to an exhaust region. In certain aspects, the gas analyzer includes a temperature sensor adapted to measure a temperature of the air flowing in the proximity of the flow channel, and a pressure sensor adapted to measure a pressure of the air flowing in the proximity of the flow channel. In certain aspects, the gas analyzer further includes a second temperature sensor located proximal to the exhaust region, wherein the first temperature sensor is located proximal to the intake region. In certain aspects, the air flow device creates flow rates within the flow channel of greater than about 5-6 liters per minute (lpm), and in certain aspects, greater than about 3000 lpm. In certain aspects, the diameter, or other dimension, of the flow channel is greater than about 0.5 cm, and in certain aspects it is greater than about 1 cm, or greater than about 1 inch. In certain aspects, the intake region includes one or more openings, or one or more intake tubes each having an opening, wherein a sum of the cross-sectional areas of the openings is substantially the same as, or greater than, a minimum cross-sectional area of the flow channel. In certain aspects, the air flow device includes a low power air flow device such as a fan or a blower.

According to another embodiment, a method is provided for measuring a gas concentration in a gas measurement device having a support structure coupling a detector section with an illumination source section and forming a flow channel defining an optical path measuring region. The method typically includes pulling or pushing air through the flow channel from an intake region of the support structure using an air flow device located proximal to an exhaust region, activating an illumination source in the source section whereby an illumination beam traverses the optical path measuring region at least once, and detecting the illumination beam using a detector in the detector section. In certain aspects, the method further includes determining a concentration of a gas in the air based on characteristics of the detected illumination beam. In certain aspects, the gas includes methane or ammonia or other sticky or reactive gas. In certain aspects, the air flow device includes a low power air flow device such as a fan or a blower.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION

Various embodiments provide systems and methods for measuring densities of gasses such as $CO_2$, $CH_4$, $N_2O$, $NH_3$, isotopes of $CO_2$ and $H_2O$, etc. The systems and methods are particularly useful in turbulent air structures. For example, in certain embodiments, the systems and methods advantageously sample and measure gas concentration, temperature and pressure at high speed and at high bandwidth, and allow for eddy covariance calculations and calculation of dry mole fraction, or mixing ratio (or other similar units) of gas components.

Operational Overview

Gas analyzers according to various embodiments generally include a light source, a sample or flow cell, and a detector. The gas analyzers disclosed herein can be used to measure a concentration of one or more gases that have a high absorbance at different wavelength bands. For example, in one application, a gas analyzer can be used to measure a concentration of $CO_2$ and water vapor ($H_2O$) in a sample gas, typically air. The gas analyzers are also able to measure a concentration of other gases such as $CH_4$, $N_2O$, $NH_3$, isotopes of $CO_2$, etc. In particular, embodiments herein are useful for measuring "sticky" gases, or gases that tend to be reactive, such as ammonia, volatile organic compounds, etc. Generally, the gas analyzers use non-dispersive infrared (NDIR) absorption or lasers to measure concentration of a gas in a sample cell based on the difference between absorption of radiation passing through the sample cell and a reference cell, or against a calibrated reference signal. Advantageously, the gas analyzers do not require long intake tubes and are capable of taking high speed measurements which enable, inter alia, calculation of dry mole fraction, or mixing ratio (or similar units) of gas components.

In operation, a light source transmits light having a spectrum of wavelengths through sample and reference cells. Gases present in the sample cell absorb light at different wavelength bands. For example, $CO_2$ has a high absorbance at 4.255 µm, and water vapor has a high absorbance at 2.595

µm. Light exiting the sample cell is detected by the detector, which is sensitive to wavelength bands absorbed by the gases (e.g., $CO_2$ and $H_2O$), or two detectors can be used, each sensitive to the wavelength band absorbed by one of the gases. The concentration of the gases in the sample cell can be determined by calculating the difference between absorption in the sample cell and the reference cell or a reference signal. For example, when a reference cell contains a non-absorber gas, the signal detected in the sample cell is compared to the signal detected in the reference cell to provide an absolute measurement of gas concentration in the sample cell. Reactive gases such as ammonia, volatile organic compounds, or other gases can be similarly measured and detected. It should be appreciated that a reference cell is not required and that other techniques may be used. For example, an optical filter disk can be used to measure light intensity at a wavelength close to the wavelength of interest, but which does not absorb the gas species of interest. Also, a feedback mechanism to keep the light source (e.g., laser) locked at a specific frequency may be used. One example would be a source of pure $CH_4$ that can be used, not to measure absorbance, but rather to keep the light source locked on the desired wavelength through a feedback mechanism. It should also be appreciated that other types of spectroscopy measurement methods may be used, for example, tunable diode laser spectroscopy (TDLS), wavelength modulation spectroscopy (WMS) and others as are well known. U.S. Pat. Nos. 6,317,212, 6,369,387, 8,125,626 and 8,130,379, which are each hereby incorporated by reference in its entirety, disclose various useful features of open and closed path gas analyzers, including optical filter configurations and techniques.

Figure 1:
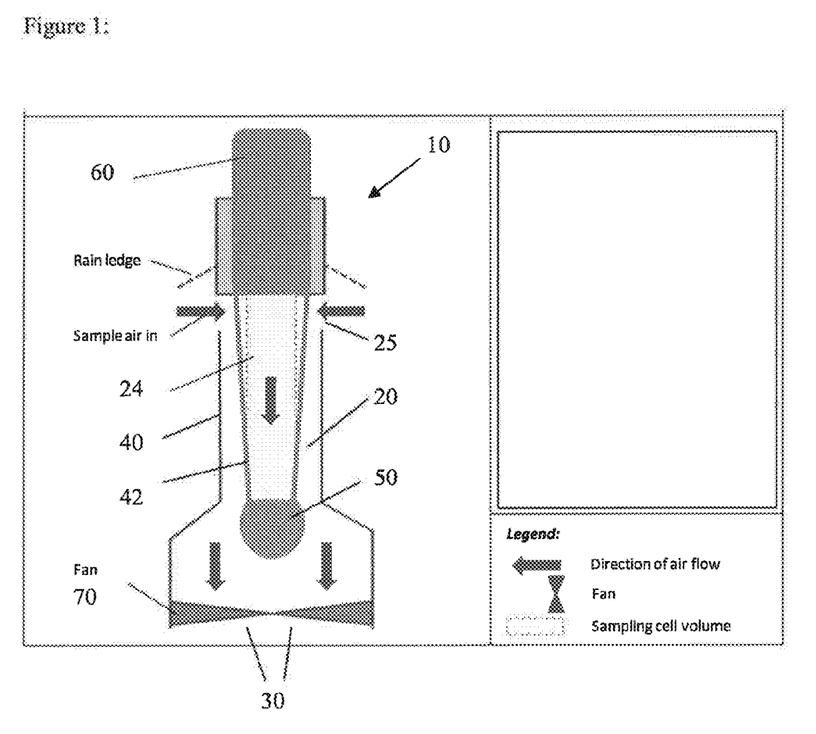
FIG. 1 illustrates a side cross-sectional view of a gas analyzer according to one embodiment.

FIG. 1 illustrates a side cross-sectional view of a gas analyzer 10 according to one embodiment. Gas analyzer 10 includes an air flow region or flow channel 20 defined by the housing structure or support structure 40 according to one embodiment. As shown, housing structure 40 defines a cylindrical gas flow path which has two openings at either end, a gas intake region 25 and a gas exhaust region 30. In operation, gas enters intake region 25, flows through the flow channel 20 defined by cylindrical portion 40 and exits exhaust region 30. In one embodiment, a low-power fan 70, or other low power air-flow device, operates to pull air through the flow channel 20 from the intake region 25 where it exits at the exhaust region 30. A blower may be used in some embodiments to push or pull air through the flow channel. Gas intake region 25 may include a single intake port, or a tube, or multiple ports or tubes. For example, as shown, substantially the entire circumference of the cylindrical region 25 may be open (to define an intake port) to allow air to enter the device from all sides. In certain aspects, the fan, or other low power device, enables pulling air through the flow channel at rates of greater than 5 or 6 liters per minute (lpm), and advantageously at rates from 10 to 100 lpm, and even 100 to 600 lpm and much greater at relatively low power consumption. Table I, below, shows minimum flow rates needed for 10 Hz air sampling of given cell volume.

TABLE I

Calculations of minimum flow rates needed for 10 Hz air sampling of given cell volume. As seen from the table, present instruments are mostly designed for small cell sampling. Various embodiments herein overcome this limit and enable rapid sampling in large cells.

| Cell Volume | Flow rate | Present gas analyzers |
|---|---|---|
| 10 cm3 | 6 lpm | LI-7000, LI-7200 |
| 50 cm3 | 30 lpm | CSI, Picarro, LosGatos methane and isotope gas analyzers, but with serious deficiencies- |
| 100 cm3 | 60 lpm | Embodiments herein enable same measurements without such deficiencies |
| 500 cm3 | 300 lpm | None. Embodiments herein enable sampling this fast |
| 1 liter | 600 lpm | None. Embodiments herein enable sampling this fast |
| 2 liter | 1200 lpm | None. Embodiments herein enable sampling this fast |
| 3 liter | 1800 lpm | None. Embodiments herein enable sampling this fast |
| 4 liter | 2400 lpm* | None. Embodiments herein enable sampling this fast |
| 5 liter | 3000 lpm | None. Embodiments herein enable sampling this fast |
| 6 liter | 3600 lpm | None. Embodiments herein enable sampling this fast |
| 7 liter | 4200 lpm | None. Embodiments herein enable sampling this fast |
| 8 liter | 4800 lpm | None. Embodiments herein enable sampling this fast |

Support structure 40, in one embodiment, includes a source section or portion 60 that houses a light or radiation source and associated electrical and optical components, and a detector section or portion 50 that houses one or more detectors and associated optical and electrical components. As shown, source section 60 may be coupled with detector section 50 via one or more struts or rods 42, which may house or enclose electrical connectors/wires to enable communication to/from section 50. Optical windows (not shown) are provided in one embodiment proximal to source section 60 and detector section 50 to allow for an air-tight seal of these sections. The optical windows allow light of a desired wavelength range to pass (e.g., from source and to the detector). In typical operation, light (typically IR light, laser light, etc.) emanating from source portion 60 travels to detector portion 50 within and along an optical path measuring region 24 defined by the optical windows or by the source and detector sections. In one embodiment, an O-ring is provided proximal the optical windows to provide a more robust. Section 50 or section 60 could hold a reference cell, depending on the application.

It should be appreciated that section 60 could hold a detector and associated components and that section 50 could house the light source and associated components. It should also be appreciated that the source and detector could both be located within the same section, e.g., within section 50 or within section 60. In this case, a mirror element (or other optical element that reflects light or refracts light or otherwise redirects light) is positioned on the opposite section (e.g., in place of an optical window), so that light emanating from the source travels through the optical path measuring region 24, reflects off of the mirror element and returns along optical path measuring region 24 to the detector. Useful light or radiation sources include narrow band sources such as lasers and LEDs, or broadband sources such as arc lamps, as well as components such as filters to allow for selection of wavelength(s) when desired. Useful detectors include photodiodes, avalanche diodes, PMTs or other detectors as would be apparent to one skilled in the art depending on the particular application.

Figure 2:
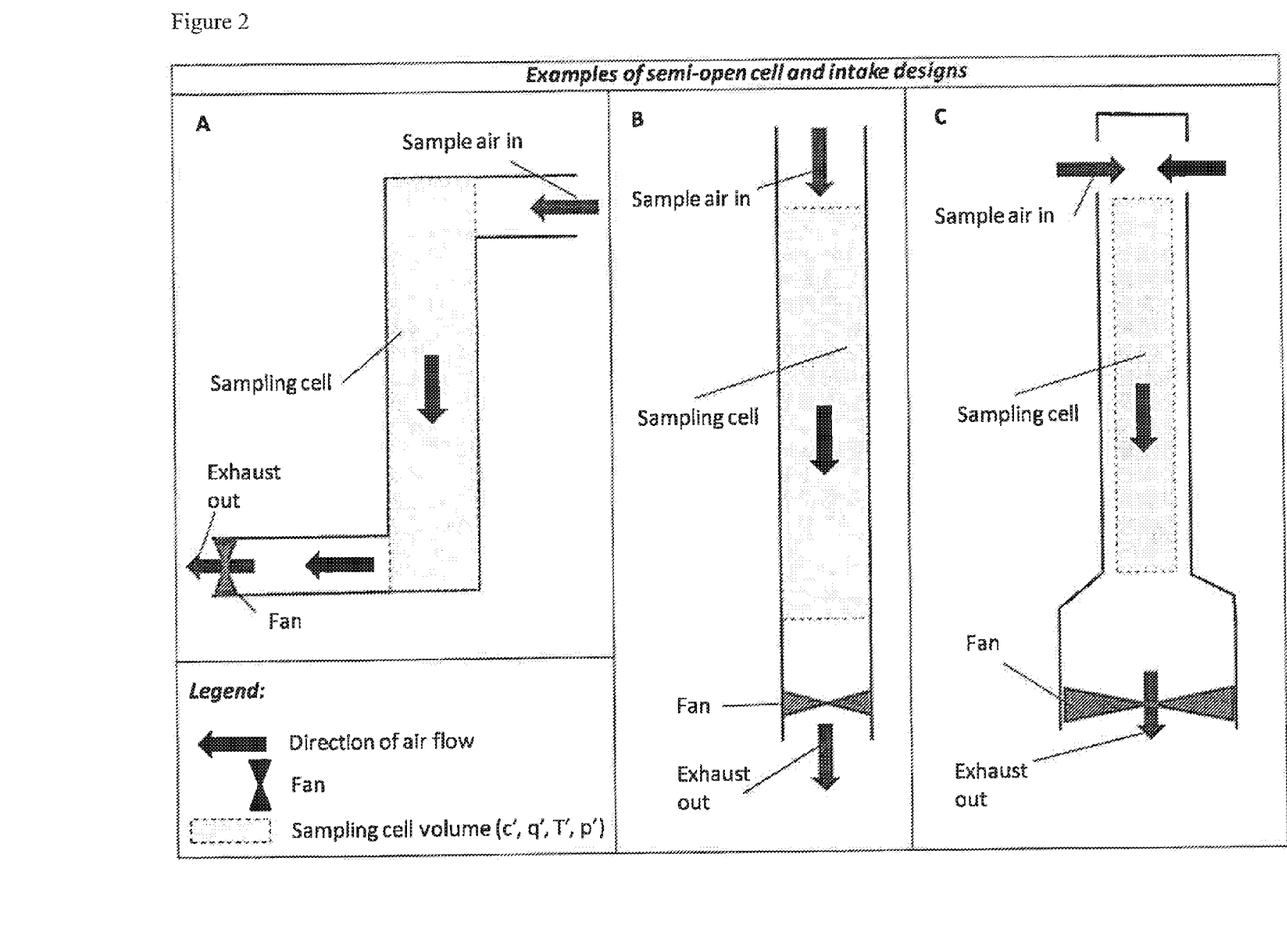
FIG. 2 illustrates exemplary gas analyzer sampling cell designs according to various embodiments.

FIG. 2 illustrates exemplary gas analyzer sampling cell designs according to various embodiments. As shown in FIG.

2A, the intake region and exhaust region of the support structure both include tubes that are each 90 degrees relative to an axis of the flow channel (sampling cell); that is the angle of intake and the angle of exhaust are 90 degrees relative to the flow channel. As shown in FIG. 2B the intake region and exhaust region of the support structure are in line with the axis of the flow channel; that is, the angle of intake and the angle of exhaust are co-linear or coaxial with the flow channel. In FIG. 2B, which is similar to the design of FIG. 1, the intake region of the support structure is 90 degrees relative to an axis of the flow channel (sampling cell) and the exhaust region is in line with the flow channel. It should be understood that the angle of intake or the angle of exhaust need not be 90 degrees or coaxial in relation to the flow channel, but that other intake and exhaust angles are contemplated. Multiple other arrangements are also possible.

Returning to FIG. 1, support structure 40 (including internal struts 42) couples the detector section with the source section and defines an optical path measuring region within the flow channel. In some embodiments, the optical path measuring region is physically between the source section and the detector section, and in other embodiments, the optical path measuring region is proximal to the detector and source sections (e.g., the source and detector are arranged near to each other on one side of the optical path measuring region and a mirror is positioned at an opposite side whereby an illumination beam from the source reflects off of the mirror and is detected by the detector after making two passes through the optical path measuring region). In one arrangement, as an example, the source and detector sections may be positioned adjacent each other, and a mirror may be positioned a certain distance from the source and detector and oriented so as to reflect light from the source to the detector; hence, the path measuring region of this configuration would include the source-to-mirror segment and the mirror-to-detector segment. In some embodiments, the source and detector are arranged or held by the housing structure such that the path of the laser has a direction component that is perpendicular to the direction of airflow in the flow channel, i.e., the path of the laser light is at an angle relative to the axis of the flow channel. For example, the laser beam may be entirely perpendicular, or it may traverse the flow channel at an angle relative to the direction of airflow, either striking a detector, or a mirror element positioned on the opposite side of the flow channel. In certain aspects, for example, the source and detector are positioned at opposite sides of the flow channel, e.g., at positions perpendicular to the airflow such as on cylindrical structure 40 in FIG. 1. In other embodiments, the source and detector are arranged on the same side and a mirror is positioned at an opposite side whereby the illumination beam reflects off of the mirror and is detected by the detector after making two passes through the flow channel. In some embodiments, for example as shown in FIG. 1, the source and detector sections are arranged such that the path of the laser light is substantially aligned with the airflow, e.g., the laser beam is substantially parallel to the axis of the flow channel, e.g., within about 5 or 10 degrees of parallel. In certain aspects, the flow channel may be so short and/or wide that there may be no definable axis of flow, e.g., a dead volume is created. In this case the optical path can be configured to traverse the flow channel in any manner/direction.

In certain embodiments, the intake region includes a tube or opening having a dimension (e.g., diameter or minimum cross-sectional area) that is substantially the same as (e.g., slightly smaller, within 5 or 10% or so), exactly the same, or greater than, the opening of the flow channel. In other aspects, one or more openings in the support structure define the intake region, where each opening has a dimension (e.g., cross sectional area), and where the sum total of the opening dimensions (e.g., sum of the cross-sectional areas), is substantially the same as (e.g., slightly smaller, within 5 or 10% or so), exactly the same, or greater than the dimension (e.g., cross sectional area), of the flow channel. It should be appreciated that the openings and the flow channel need not have circular or elliptic cross-sections; rather the cross sections of the openings and flow channel can take on any shape, e.g., circular, elliptical, rectangular, polygonal, etc. In general a wide intake, e.g., on the order of 0.5 to 1 inch or greater is desired to minimize flow restriction and pressure drop. Also, a short intake is desirous to minimize turbulent mixing on intake, and to reduce any physical and chemical interactions between the sampled gas and the intake walls.

Temperature and Pressure Measurements

Knowing the temperature of the sample gas is important for various measurements, such as for calculating the mole fraction, dry mole fraction, mixing ratio or similar units from the number density, mass density or mole density or similar units. According to one embodiment, the temperature is measured proximal an intake 25 and proximal an exhaust 30 of the sample cell volume 20 in a manner that does not fully block the optical signal (e.g., light) in the flow channel 24. The volume average temperature ($T_{block}$) in the cell can be calculated from a relationship between the intake ($T_{in}$) and exhaust ($T_{out}$) temperatures along with the flow rate of the sample gas. In certain aspects, for example, a generic function is $T_{IRGA}=f(T_{in}, T_{out}, T_{block}, U)$, where U is the mean velocity through the cell. In certain aspects, additional temperature sensors may be used, e.g., to measure the gas temperature at different points in the flow path.

In certain embodiments, a single temperature sensor is used. For example, a single temperature sensor may be located proximal to an internal portion of the flow channel. Temperature measurements can be taken and a volume temperature can be calculated using the single temperature sensor signal and known parameters, such as flow rate, flow cell volume, etc. However, it is appreciated that the use of two (or more) temperature sensors as described above will provide a more robust and accurate temperature for the gas in the flow cell. Temperature can also be measured using an electric wire or thermocouple placed across or along the flow channel or optical channel. Laser temperature measurements and multiple other approaches to temperature measurements can be utilized.

It is also important to know the pressure in the flow cell, e.g., to facilitate calculation of mole fraction, dry mole fraction, mixing ratio or similar units from the number density, mass density or mole density or similar units. In one embodiment, a pressure sensor (not shown) is positioned to measure the pressure at an internal point within the flow channel. In one embodiment, the pressure sensor, includes a differential pressure sensor. In order to maintain the sensor head as compact as possible, in one embodiment, a coupled set of absolute/differential pressure transducers are used to obtain high frequency pressure data from the sample cell (since pressure sensor that measures absolute sensor may be quite bulky). The pressure of the gas at the interior of the flow cell can be determined by adding the differential pressure and the mean pressure. In one embodiment, the pressure sensor is a high speed pressure sensor. Useful pressure sensors include a piezoresistive silicon differential pressure transducer (e.g., MPX2010DP, Freescale Semiconductor Inc. (Motorola)) and a piezoresistive silicon absolute pressure transducer (MPX4115A, Freescale Semiconductor Inc. (Motorola)). Other pressure sensors as would be apparent to one skilled in the art may be used. Other pressure measurement arrangements are possible as long as pressure in the flow channel or in the sampling channel can be deduced.

Mole Fraction Measurement

According to one embodiment, mole fraction, dry mole fraction, mixing ratio or similar units is determined using a gas analyzer according to the various embodiments disclosed herein. Advantageously, gas analyzers as disclosed herein are capable of making dry mole fraction measurements at high bandwidth in real time (or during post processing). For example, it is desirable to determine a dry mole fraction of $CO_2$ or other gas component at a certain frequency response, e.g., 10 Hz. In order to provide this output, the following steps occur according to one embodiment. First, a flow rate is introduced through the flow channel of the IRGA that purges the volume, for example, at about a 10 Hz or greater purge rate. For example, a flow of ambient air into the intake region, through the flow cell and out the exhaust is initiated at the desired flow rate. The temperature is then measured, e.g., at the intake and at the exhaust, with a frequency response similar to the volume-average. The pressure (e.g., differential pressure) is measured at a point interior, e.g., within the flow channel, with a similar frequency response to the other measurements. The temperature measurements are taken substantially simultaneously with each other and with the pressure measurement. The temperature measurements can be corrected for spatial separation (e.g., $T_A$(t+delay) and $T_C$(t-delay) where the delay is a function of the flow rate and flow path/IRGA geometry). Simultaneously with these measurements, the detector system is determining concentration of gas components (e.g., carbon dioxide and water vapor). In certain aspects, the bandwidth of all the signals (e.g., temperature, pressure, absorbance) is matched to the physical time constant of the flow through the flow cell volume (i.e., flow rate divided by volume). U.S. Pat. No. 8,125,626, which is hereby incorporated by reference, illustrates exemplary calculations for determining the dry mole fraction. Once determined, the dry mole fraction may be returned, e.g., displayed or stored for later use.

It should be understood that, herein and elsewhere, when referring to a mole fraction (e.g., $CO_2$ mole fraction) that includes water vapor, the term "mole fraction" is typically used; when referring to a mole fraction after water vapor is removed, the term "dry mole fraction" is typically used, and in certain instances the term "instantaneous mole fraction" or "instantaneous dry mole fraction," "mole fraction," "mixing ratio" or other similar units may be used to refer to high speed measurements. It also should be appreciated that fast temperature and fast pressure measurements are not required, but enhance the performance. Fast temperature and pressure may be measured outside the proposed device with a different device(s) which may result in increased uncertainty of the measurements, but will not invalidate the measurements.

EXAMPLES

Figure 3:
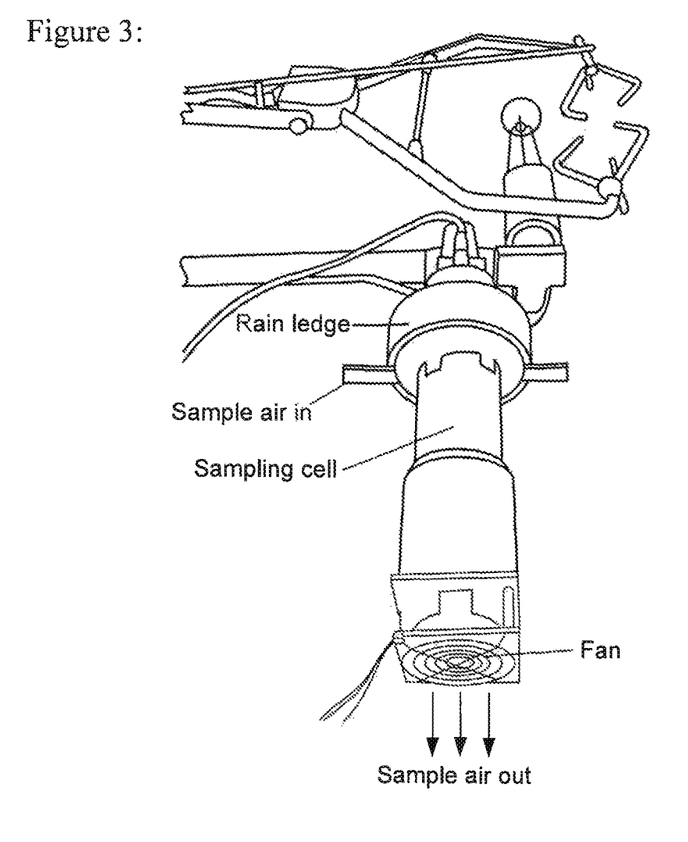
FIG. 3 illustrates a photograph of a prototype gas analyzer according to one embodiment.

FIG. 3 illustrates a photograph of a prototype gas analyzer according to one embodiment; the gas analyzer (bottom) is installed and working next to a LI-7500 instrument (top background; from Li-Cor Biosciences) and a sonic anemometer (top foreground).

Figure 4:
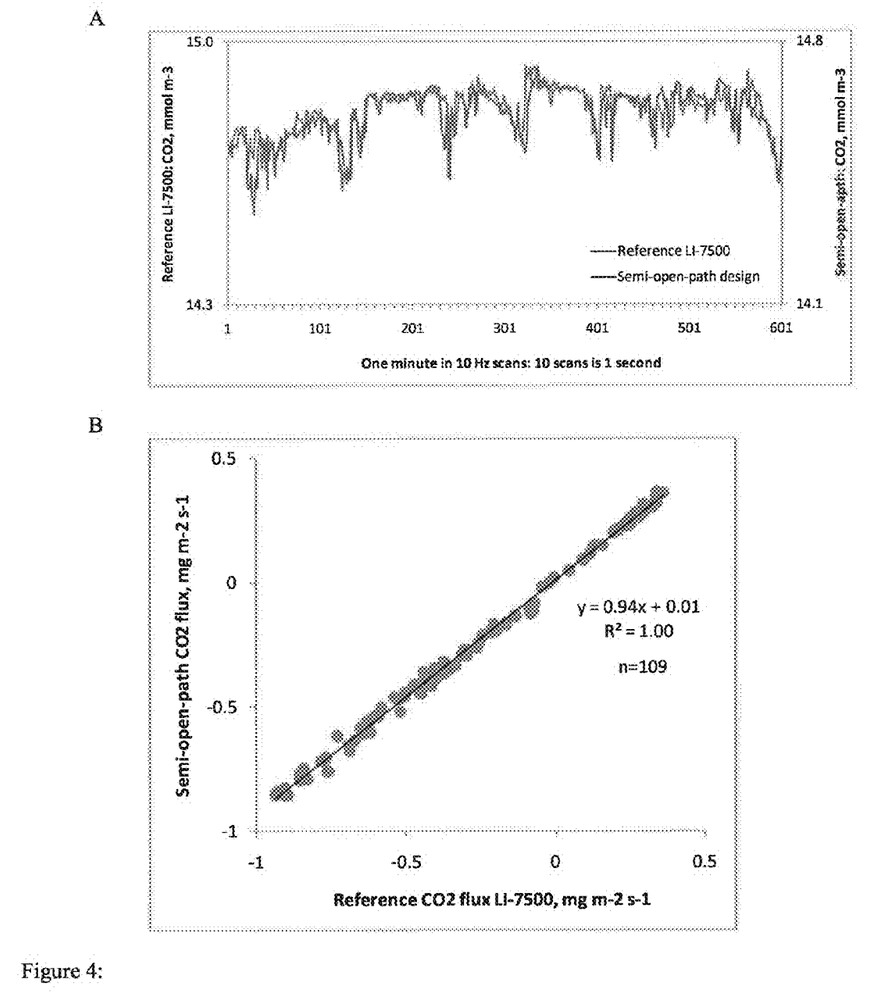
FIG. 4(A) illustrates an example of instantaneous time series of $CO_2$ concentrations measured with a LI-7500 reference instrument and measured with proposed semi-open-path analyzer prototype.
FIG. 4(B) shows results of the comparison of raw volume-averaging-corrected $CO_2$ fluxes measured with the LI-7500 instrument and measured with a semi-open-path analyzer embodiment. A flow rate of 2400 lpm was provided by a low-power 12V fan. Both instantaneous time series and fluxes from the semi-open-path design were within a few percent from those measured by the LI-7500 reference, proving the practicality and good performance of the embodiment.

FIG. 4(A) illustrates an example of instantaneous time series of $CO_2$ concentrations measured with the LI-7500 instrument and measured with a semi-open-path analyzer embodiment. FIG. 4(B) shows results of the comparison of raw volume-averaging-corrected $CO_2$ fluxes measured with the LI-7500 instrument and measured with the semi-open-path analyzer embodiment. A flow rate of 2400 lpm was provided by a low-power 12V fan. Both instantaneous time series and fluxes from the semi-open-path design were within a few percent from those measured by the LI-7500 reference, proving the practicality and good performance of the embodiment used.

It should be appreciated that the gas analysis processes described herein may be implemented in computer code running on a processor of a computer system. The code includes instructions for controlling a processor to implement various aspects and steps of the gas analysis processes. The code is typically stored on a hard disk, RAM or portable medium such as a CD, DVD, etc. Similarly, the processes may be implemented in a gas analyzer including an intelligence module, typically having one or more processors executing instructions stored in a memory unit coupled to the processor(s). The intelligence module may be part of the gas analyzer, or part of a separate system directly or indirectly coupled with the gas analyzer. Code including such instructions may be downloaded to the system or gas analyzer memory unit over a network connection or direct connection to a code source or using a portable, non-transitory computer-readable or processor-readable medium as is well known.

One skilled in the art should appreciate that the processes of the present invention can be coded using a variety of programming languages such as C, C++, C#, Fortran, VisualBasic, etc., as well as applications such as Mathematica® which provide pre-packaged routines, functions and procedures useful for data visualization and analysis. Another example of the latter is MATLAB®.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A gas analyzer comprising:
a) a detector section including a detector;
b) a source section including a light source;
c) a support structure coupling the detector section with the source section and forming a flow channel defining an optical path measuring region enclosed within one or more walls of the support structure; and
d) an air flow device configured to pull air through the flow channel from an intake region in the support structure to an exhaust region,
wherein the intake region includes one or more air intake openings in the one or more walls of the support structure, wherein a sum of cross-sectional areas of the intake openings is substantially the same as, or greater than, a minimum cross-sectional area of the flow channel.

2. The gas analyzer of claim 1, further including:
a first temperature sensor adapted to measure a temperature of the air flowing in flow channel; and
a pressure sensor adapted to measure a pressure of the air flowing in the flow channel.

3. The gas analyzer of claim 2, further including a second temperature sensor located proximal to the exhaust region, wherein the first temperature sensor is located proximal to the intake region.

4. The gas analyzer of claim 2, wherein the pressure sensor is a high speed pressure sensor.

5. The gas analyzer of claim 1, wherein the detector section and the source section each include an optical window or other element that allows light of a desired wavelength range to pass.

6. The gas analyzer of claim 1, wherein the support structure holds the detector section and source sections opposite each other along an axis substantially parallel to an axis of the flow channel.

7. The gas analyzer of claim 1, wherein the support structure holds the detector section and source sections opposite each other along an axis having a direction component that is perpendicular to an axis of the flow channel.

8. The gas analyzer of claim 1, wherein the air flow device creates flow rates greater than about 30 liters per minute (lpm) within the flow channel.

9. The gas analyzer of claim 1, wherein a diameter of the flow channel is greater than about 0.5 cm.

10. The gas analyzer of claim 9, wherein the intake region includes an intake tube having a diameter that is substantially the same as or greater than, the diameter of the flow channel.

11. The gas analyzer of claim 1, wherein the air flow device includes a fan or a blower.

12. The gas analyzer of claim 1, wherein the air flow device includes a low power air flow device.

13. The gas analyzer of claim 1, wherein the air flow device is located proximal to the exhaust region.

14. A method of measuring a gas concentration in a gas measurement device having a support structure coupling a detector section with an illumination source section and a flow channel defining an optical path measuring region enclosed within one or more walls of the support structure, the method comprising:
   pulling air through the flow channel from an intake region of the support structure using a low power air flow device located proximal to an exhaust region, wherein the intake region includes one or more air intake openings in the one or more walls of the support structure, wherein a sum of the cross-sectional areas of the intake openings is substantially the same as, or greater than, a minimum cross-sectional area of the flow channel;
   activating an illumination source in the source section whereby an illumination beam traverses the optical path measuring region at least one time; and
   detecting the illumination beam using a detector in the detector section.

15. The method of claim 14, further comprising:
   measuring a temperature of the air flowing in the flow channel.

16. The method of claim 14, further comprising measuring a pressure in the flow channel.

17. The method of claim 14, further including determining a concentration of a gas or other chemical component in the air based on characteristics of the detected illumination beam.

18. The method of claim 17, wherein the gas includes methane or ammonia.

19. The method of claim 14, wherein a diameter of the flow channel is greater than about 0.5 cm.

20. The method of claim 14, wherein the flow of air has a flow rate of about 30 lpm or greater.

\* \* \* \* \*